US010806395B2

(12) United States Patent
Borsook et al.

(10) Patent No.: US 10,806,395 B2
(45) Date of Patent: Oct. 20, 2020

(54) PAIN DETECTION SYSTEM AND METHOD UTILIZING NEAR-INFRARED SPECTROSCOPY

(71) Applicant: Children's Medical Center Corporation, Boston, MA (US)

(72) Inventors: David Borsook, Concord, MA (US); Lino Becerra, Concord, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/777,323

(22) PCT Filed: Mar. 13, 2014

(86) PCT No.: PCT/US2014/026820
§ 371 (c)(1),
(2) Date: Sep. 15, 2015

(87) PCT Pub. No.: WO2014/152020
PCT Pub. Date: Sep. 25, 2014

(65) Prior Publication Data
US 2016/0015316 A1 Jan. 21, 2016

Related U.S. Application Data

(60) Provisional application No. 61/801,412, filed on Mar. 15, 2013.

(51) Int. Cl.
*A61B 5/00* (2006.01)
*A61B 5/1455* (2006.01)
*A61B 5/145* (2006.01)

(52) U.S. Cl.
CPC .......... *A61B 5/4824* (2013.01); *A61B 5/0075* (2013.01); *A61B 5/0086* (2013.01);
(Continued)

(58) Field of Classification Search
CPC ... A61B 5/4824; A61B 5/0075; A61B 5/0086; A61B 5/14546; A61B 5/14551; A61B 5/4005; A61B 5/4064; A61B 5/4848
See application file for complete search history.

(56) References Cited

U.S. PATENT DOCUMENTS 7,899,524 B2 * 3/2011 Kozel ................. A61B 5/164
600/410
2005/0209317 A1 * 9/2005 Apkarian .............. A61K 31/198
514/471
(Continued)

OTHER PUBLICATIONS

"HOMER2 Users's Guide" (Year: 2012).*
(Continued)

*Primary Examiner* — Joanne M Hoffman
(74) *Attorney, Agent, or Firm* — Mintz Levin Cohn Ferris GLovsky and Popeo, P.C.; Peter F. Corless (57) ABSTRACT

Disclosed is a pain detection system and method. Preferred methods include capturing imaging data from patient using functional near-infrared spectroscopy. In methods of the invention, pain may be assessed from a non-responsive patient. Preferred methods may further include measuring hemodynamic parameters using the optical imaging data and averaging the measured hemodynamic parameters to reduce background noise. Additionally, a pattern in the averaged hemodynamic parameters is identified and the pattern is compared to a predetermined associated with patient pain. The method further includes detecting, by the processor, a similarity between the pattern and the predetermined pattern and outputting a signal indicating patient pain.

13 Claims, 6 Drawing Sheets

(52) U.S. Cl.
CPC ...... *A61B 5/14546* (2013.01); *A61B 5/14551* (2013.01); *A61B 5/4005* (2013.01); *A61B 5/4064* (2013.01); *A61B 5/4848* (2013.01); *A61B 5/0042* (2013.01)

(56) References Cited

U.S. PATENT DOCUMENTS

| | | |
|---|---|---|
| 2008/0249430 A1 | 10/2008 | John et al. |
| 2009/0054955 A1 | 2/2009 | Kopell et al. |
| 2010/0217138 A1* | 8/2010 | Borsook .............. A61B 5/0261 600/504 |
| 2011/0066078 A1* | 3/2011 | Sarvazyan ............... A61B 5/16 600/587 |
| 2011/0118661 A1 | 5/2011 | Pless et al. |
| 2011/0152249 A1* | 6/2011 | Borsook .............. A61B 5/1455 514/217 |
| 2011/0245708 A1 | 10/2011 | Finkel et al. |

OTHER PUBLICATIONS

Amarnath, "Investigation of frontopolar cortex under noxious pain stimuli using functional near infrared spectroscopy", Biomedical Optics and 3D Imaging OSA, 2012, pp. 1-3 (Year: 2012).*
International Search Report issued in corresponding International Application Ser. No. PCT/US2014/026820, dated Jul. 30, 2014, 3 pages.

* cited by examiner

PAIN DETECTION SYSTEM AND METHOD UTILIZING NEAR-INFRARED SPECTROSCOPY

CROSS-REFERENCE TO RELATED APPLICATIONS

This application is the U.S. national stage pursuant to 35 U.S.C. § 371, of U.S. international application Ser. No. PCT/US2014/026820, filed Mar. 13, 2014, designating the United States and published in English on Sep. 25, 2014 as publication WO 2014/152020 A1, which claims priority to, and the benefit under 35 U.S.C. § 119(e) of U.S. provisional patent application No. 61/801,412, filed Mar. 15, 2013. The entire contents of the aforementioned patent applications are incorporated herein by this reference.

TECHNICAL FIELD

In one aspect, systems and methods are provided that detect patient pain during a medical procedure by monitoring the patient throughout the procedure using functional near-infrared spectroscopy.

BACKGROUND

Many types of medical procedures involve the use of anesthetics, analgesics, and other sedation or partial sedation methods. For example, sedatives are administered before a colonoscopy procedure to reduce anxiety in a patient and reduce discomfort during the procedure. During a colonoscopy procedure many patients report having experienced pain. The pain experienced during the procedure has been observed by practitioners through patient movement or grimacing and may be due to residual effects of the sedative and/or analgesic agent and gender differences. Thus, research implies that nociceptive pathways may be activated during the procedure due to stimuli causing local or central neuronal sensitization and potentially leading to postoperative pain. Routine colonoscopy procedures may be used to evaluate pain signals during a procedure when a patient is under sedation because patient behaviors such as grimacing, moaning, or movement may be an indicator of experienced pain.

Various approaches to minimizing pain during medical procedures have been developed and include the use of carbon dioxide for insufflation, improving anesthetic regimens, providing technical aids, and patient controlled sedation or analgesia. However, precise dose administration of anesthetics may be difficult since dose is determined by a patient's age, medical history, current medications, previous use of anesthetics, current condition (e.g., unstable or critical), and the like. In addition, the time of administering the anesthetics and commencing the medical procedure may vary thereby potentially causing insufficient time for the drugs to take effect. As an example, functional magnetic resonance imaging (fMRI) may capture brain activity associated with pain. However, fMRI is often difficult to use due to equipment unavailability, relatively large physical sizes, and relatively high operating costs among other reasons.

SUMMARY

We now provide new pain recognition systems and methods utilizing a functional near-infrared spectroscopy system. Preferred systems and methods are configured to detect pain experienced during a medical procedure while a patient is sedated or under other forms of anesthesia using near-infrared spectroscopy (NIRS) system.

In particular systems and methods, a functional near-infrared spectroscopy (NIRS or fNIRS) system is utilized as the imaging system.

Preferred methods of the invention include recognizing pain in a non-responsive patient, comprising obtaining functional near-infrared spectroscopy imaging data from a non-responsive patient to recognize pain in the patient.

In particular systems and methods, the patient is non-responsive, particularly nonresponsive to commands, such as in a controlled state of anesthesia or an unconscious sedated state, or is otherwise non-responsive to commands, such as may be exhibited by a comatose patient, an infant, and the like.

In additional particular aspects, systems and methods are provided that detect pain based on pain indicia or control data obtained from a subject. This indicia or control data may be e.g. suitably obtained prior to a patient or subject becoming unresponsive, such as through sedation. For example, pain can be detected by a responsive patient or subject through any number of exercises. The patient then may be rendered non-responsive (e.g. through sedation), and the control data or pain indicia is then employed to monitor and recognize pain in the unresponsive patient.

In preferred aspects, the NIRS system can probe or detect changes in brain hemodynamic responses using infrared light wherein changes in the relative concentration of oxygenated and deoxygenated hemoglobin in the cortex indicates pain experienced by a subject, such as a patient undergoing a medical procedure.

Preferred methods include obtaining or capturing imaging data from subject, e.g. a nonresponsive patient, over a period of time (e.g. up to about 0.1, 0.5, 1, 2, 3, 5 or 10 minutes, or more) using near-infrared spectroscopy. Particularly preferred methods include obtaining or capturing optical imaging data from at least one cortical region of the brain of a subject, e.g. a non-responsive patient, over a period of time (e.g. up to about 0.1, 0.5, 1, 2, 3, 5 or 10 minutes, or more) using functional near-infrared spectroscopy. In addition, using the imaging data, preferred methods may include measuring a plurality of hemodynamic parameters, which may include oxygenated hemoglobin, deoxygenated hemoglobin, and/or total hemoglobin, in the at least one cortical region of the brain of the non-responsive patient and preferably averaging the measured plurality of hemodynamic parameters to reduce background noise. A pattern may also be identified in the averaged hemodynamic parameters which may be compared to at least one predetermined pattern associated with patient pain. When a similarity is detected between the pattern and the predetermined pattern, a signal may be output indicating patient pain. In addition, measuring the hemodynamic parameters may include measuring oxygenated and deoxygenated hemoglobin to measure blood flow.

Preferred methods may include performing an analysis exercise such as a finger tapping exercise and a variation of electrical stimulus on a non-responsive patient (e.g. a sedated patient) to inflict a level of pain. In addition, the predetermined pattern that indicated pain may comprise a plurality of peaks in the blood flow over time, wherein the method may include determining whether a time delay between performing the various activities (e.g., finger tapping exercise and the variation of electrical stimulus) and the point at which a peak occurs indicates patient pain. The predetermined pattern associated with pain may be obtained from control data for the hemodynamic parameters, wherein the control data is obtained by acquiring the optical imaging data from the at least one cortical region of the brain of a conscious patient. The optical imaging data may be obtained when the patient is not subject anesthetics and may be acquired from a finger tapping exercise and a variation of electrical stimulus. The method may further include administering an anesthetic regimen based on a particular medical procedure toward the patient after obtaining the control data.

Additionally, preferred systems may include a functional near-infrared spectroscopy configured to capture at least one cortical region of the brain of the patient over a period of time and a processor. The cortical region of the brain may be the somatosensory cortex and the prefrontal cortex. The processor may be configured to measure a plurality of hemodynamic parameters, which may include oxygenated hemoglobin, deoxygenated hemoglobin, and/or total hemoglobin, in the cortical region of the brain of the patient, using the optical imaging data.

Furthermore, the processor may be configured to average the measured hemodynamic parameters to reduce background noise and then may identify a pattern in the averaged hemodynamic parameters. The processor may then compare the pattern to at least one predetermined pattern associated with patient pain and detect a similarity between the pattern and the predetermined pattern. Additionally, the processor may be configured to output a signal indicating patient pain. The processor may be configured e.g. to control an analysis exercise such as a finger tapping exercise and a variation of electrical stimulus on the patient to inflict a level of pain toward the patient from which measurements may be obtained. Further, the processor may be configured to determine whether a time delay between performing the analysis exercise such as a finger tapping exercise and the variations of electrical stimulus and a point when a peak occurs in blood flow indicates pain in the patient.

Methods are also provided that evaluate a treatment and include administering, by a processor, the treatment toward a patient and applying a stimulus toward the patient. Such methods also may include acquiring, with a functional near-infrared spectroscopy, imaging data during the application of the stimulus. Furthermore, from the imaging data, brain activity data representing a hemodynamic parameter in at least one cortical region of the brain of the patient may be determined. The brain activity data may then be compared, by the processor, to control data which may be acquired using the functional near-infrared spectroscopy prior to the imaging data and further outputting an indication of patient pain. A reduction in intensity of the hemodynamic parameter from the control data to the imaging data may indicate a relative efficiency of the treatment as a pain-relieving treatment.

Other aspects of the invention are disclosed infra.

BRIEF DESCRIPTION OF THE DRAWINGS

The disclosure will hereinafter be described with reference to the accompanying drawings, wherein like reference numerals denote like elements, and.

DETAILED DESCRIPTION

Pain recognition systems and methods are provided that are suitably used to measure pain experienced in a medical procedure, particularly while a patient is unresponsive to commands or communication, such as resulting from sedation. Pain is measured through near-infrared spectroscopy imaging of the patient.

Methods and systems of the invention are particularly useful for a wide variety of medical procedures, including where a patient is sedated to an unconscious or unresponsive state. In the unresponsive state, pain can be assessed and e.g. an anesthetic regimen can be administered based on that pain assessment through the course of the medical procedure. The present pain detection systems and methods can provide continuous monitoring of neural activity related to pain experienced during medical procedures. The present systems and methods also may provide control of analgesic load to improve patient intraoperative comfort and decrease postoperative pain. In addition, the measure or detection of pain may be used to evaluate the effectiveness of pharmaceuticals for a variety of conditions, including e.g. irritable bowel syndrome.

Preferably functional near-infrared spectroscopy (fNIRS) is employed for imaging of the patient. Functional near-infrared spectroscopy can allow functional imaging of brain activity (or activation) through monitoring of blood oxygenation and blood volume, including in patient's cortex. Imaging can be performed in the near-infrared range such as between 700-1000 nm.

In particular methods and systems, the patient is in a non-responsive state, such as an unconscious sedated state as may be controlled by administration of anesthesia, and/or may be characterized by partial or complete loss of protective nerve reflexes, including the ability to independently breathe and respond to commands. The patient may be unable to cooperate and may have labile (fluctuating) vital signs. As referred to herein, an unresponsive patient or subject includes a subject exhibiting one or more characteristics of: 1) under the administration of anesthesia and non-responsive to commands, 2) partial or complete loss of protective nerve reflexes, such as loss of ability to i) respond to commands and/or ii) independently breathe. An unresponsive patient also may include patients in a coma or infants (who cannot respond to verbal commands).

Methods and systems of the invention also may be utilized for subject in a conscious state, including a conscious sedated state. As referred to herein, a patient in a conscious state, a conscious sedated state or other similar term is 1) capable of rational responses and/or 2) does not have altered respiratory, cardiac, and/or reflex functions (nerve reflexes from the brain) to the level that requires external support for these vital functions.

In a preferred method for recognizing pain in a non-responsive patient, steps may include obtaining functional near-infrared spectroscopy imaging data from at least one cortical region of the brain of the non-responsive patient; and comparing measured imaging data with patient pain based on control data and thereby recognizing pain in the non-responsive patient. Using the imaging data, one or more hemodynamic parameters may be measured in the at least one cortical region of the brain of the non-responsive patient. Such preferred methods may suitably comprise one or more additional steps of (i) averaging the measured plurality of hemodynamic parameters e.g. to reduce background noise; (ii) identifying a pattern in the averaged hemodynamic parameters; and/or (iii) outputting a signal indicating patient pain.

In a particular preferred method of the invention for recognizing pain in a non-responsive patient, steps may comprise obtaining functional near-infrared spectroscopy imaging data from at least one cortical region of the brain of the non-responsive patient; measuring, by a processor, using the imaging data, a plurality of hemodynamic parameters in the at least one cortical region of the brain of the non-responsive patient; averaging, by the processor, the measured plurality of hemodynamic parameters e.g. to reduce background noise; identifying, by the processor, a pattern in the averaged hemodynamic parameters; comparing, by the processor, the pattern to at least one predetermined pattern associated with patient pain based on control data; detecting, by the processor, a similarity between the pattern and the predetermined pattern; and outputting, by the processor, a signal indicating patient pain.

In such preferred methods, the hemodynamic parameters include one or more of oxygenated hemoglobin, deoxygenated hemoglobin, and total hemoglobin. Measuring at least one hemodynamic parameter may include measuring, by the processor, oxygenated and deoxygenated hemoglobin to measure blood flow. The at least one cortical region of the brain may be selected from the somatosensory cortex and the prefrontal cortex. A predetermined pattern indicating pain may comprise a plurality of sequential peaks in blood flow over time. The at least one predetermined pattern associated with pain may be obtained from the control data for the hemodynamic parameter wherein pain is detected in a conscious patient.

In another particular method for evaluating a medical treatment, steps may comprise administering a treatment to a patient; applying a stimulus to the patient; acquiring functional near-infrared spectroscopy imaging data during the application of the stimulus; determining from the imaging data, brain activity data representing a hemodynamic parameter in at least one cortical region of the brain of the patient; comparing the brain activity data representing the hemodynamic parameter to control data representing the hemodynamic parameter; and outputting an indication of patient pain. One or more of such steps may be accomplished through use of a processor.

Figure 4:
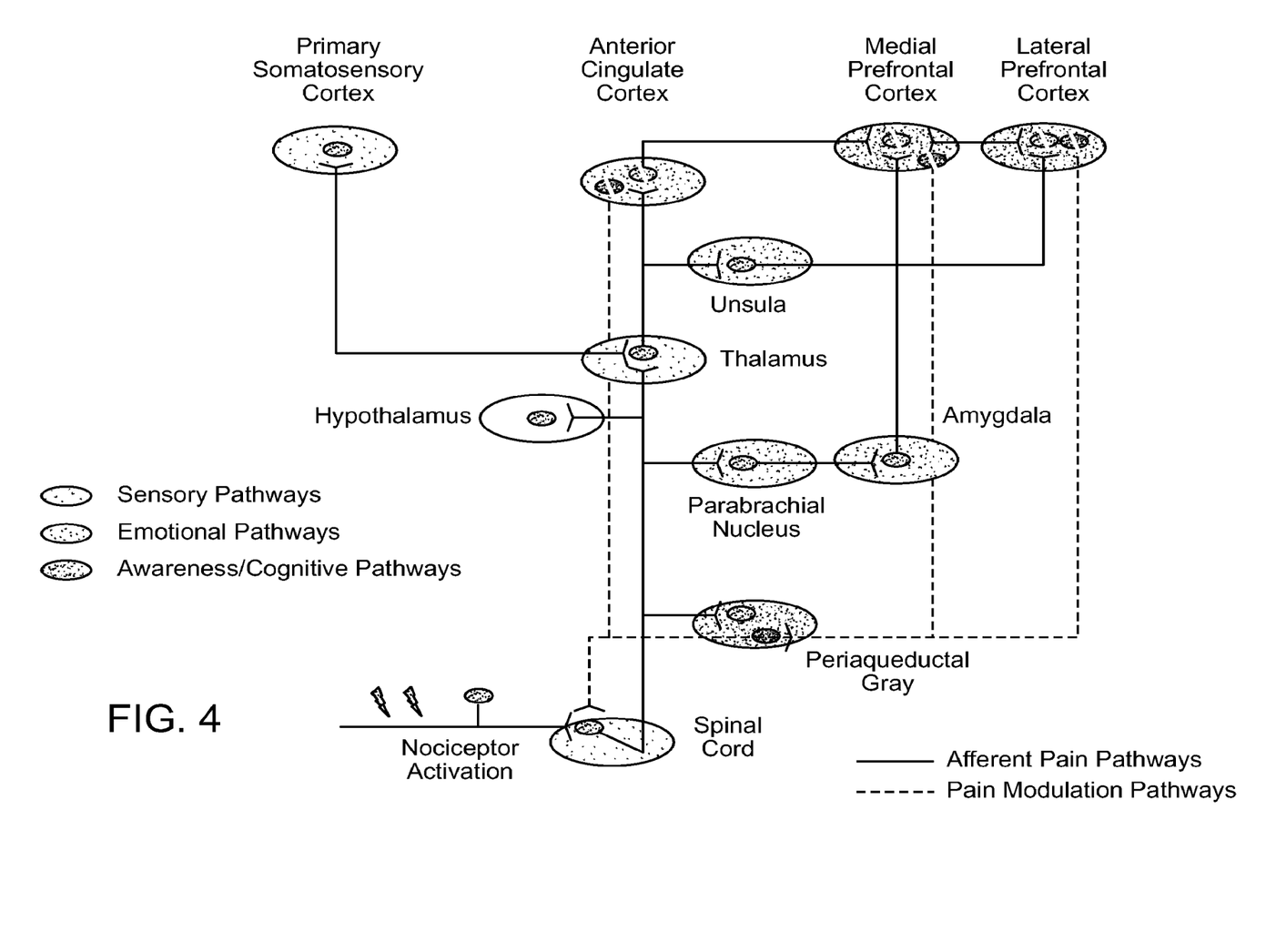
FIG. 4 illustrates exemplary pain pathways associated with the somatosensory cortex and the prefrontal cortex according to an exemplary embodiment of the present disclosure.

Referring now to the non-limiting exemplary drawings, various pain and sensory pathways may be measured in the brain using the NIRS system as shown in FIG. 4. The NIRS uses infrared light to probe changes in brain hemodynamic response, wherein near infrared light penetrates in the tissues and may traverse matter within the skull to the cortex area. A change in the relative concentration of the oxygenated hemoglobin and the deoxygenated hemoglobin in the cortex indicates a change in the number of photons that are escaping the brain.

Figure 6:
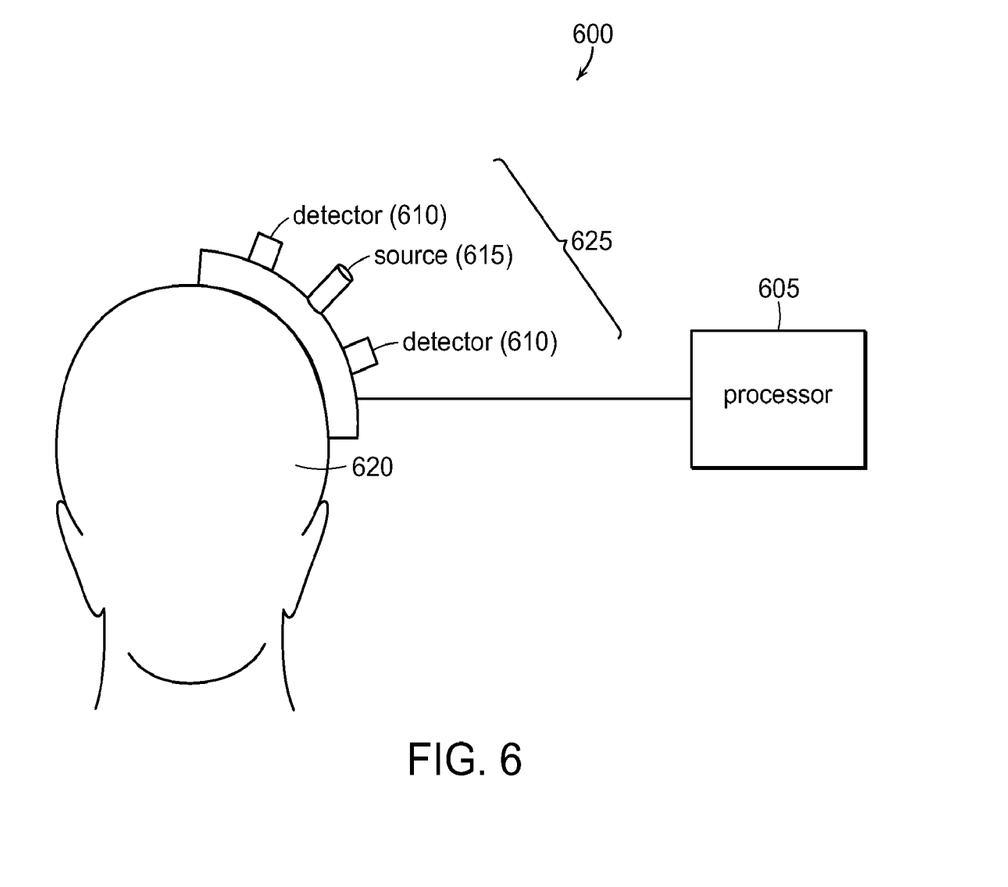
FIG. 6 illustrates an exemplary schematic diagram of the system that recognizes pain in a patent according to an exemplary embodiment of the present disclosure.

Specifically, as illustrated in FIG. 6, a functional near-infrared spectroscopy system (NIRS) 625 is a portable, non-invasive inexpensive method of monitoring hemodynamic activity at moderate depths (e.g., surface cortices). The NIRS 625 is configured to characterize relative changes in concentrations of oxygenated hemoglobin (HbO) and deoxygenated hemoglobin (HbR), which combined indicate relate change in total hemoglobin (HbT). The NIRS optodes may be fitted across predetermined cortical regions to thus monitor the hemodynamic functions caused by neuronal activity. Furthermore, since an NIRS 625 is not influenced by environmental requirements, the system may be used within an operating room. Specifically, the NIRS 625 is configured to deliver photons using fiber optics that are positioned on the head 620 of a patient and are called the source 615. In addition, other fiber cables, detectors 610, are spaced apart from the source 615 to collect the photons that are reflected from the cortical tissue. Furthermore, various detected signals may be measured to detect the intensity, the modulation depth, and the phase delay and a combination thereof may provide information regarding physiological parameters.

Furthermore, as illustrated in FIG. 6, the pain recognition system 600 may be configured to capture optical imaging data from at least one cortical region of the brain over a period of time, using the NIRS system 625. In addition, the system 600 may include a processor 605 that may be configured to measure a plurality of hemodynamic parameters in the at least one cortical region of the brain of the non-responsive patient, using the optical imaging data. The processor 605 may then be configured to average the measure plurality of hemodynamic parameters to reduce background noise in the measurement process. A pattern may then be identified in the averaged hemodynamic parameters. The processor may be configured to compare the pattern to at least one predetermined pattern associated with patient pain and a signal may be output indicating patient pain. Specifically, the predetermined pattern may be associated with control data obtained prior to a stimulus being administered to a patient. The control data may be obtained by fitting the NIRS 625 system to the patient and collecting data at point where the patient indicates experiencing pain, while the patient is conscious (e.g., is not sedated). Thus, when the patient is sedated, the control data may act as an indication of points where pain is known to exist or be experienced by the patient. Moreover, the hemodynamic parameters may include oxygenated hemoglobin, deoxygenated hemoglobin, and total hemoglobin. In addition, the at least one cortical region of the brain may be selected from the somatosensory cortex and the prefrontal cortex. The processor 605 may be further configured to control a finger tapping exercise and a variation of electrical stimulus on the patient to inflict a level of pain from which measurements may be obtained. Furthermore, the processor 605 may be configured to determine whether a time delay between performing the finger tapping exercise and the variations of electrical stimulus and a point when a peak occurs in blood flow indicates pain in the patient.

Figure 5:
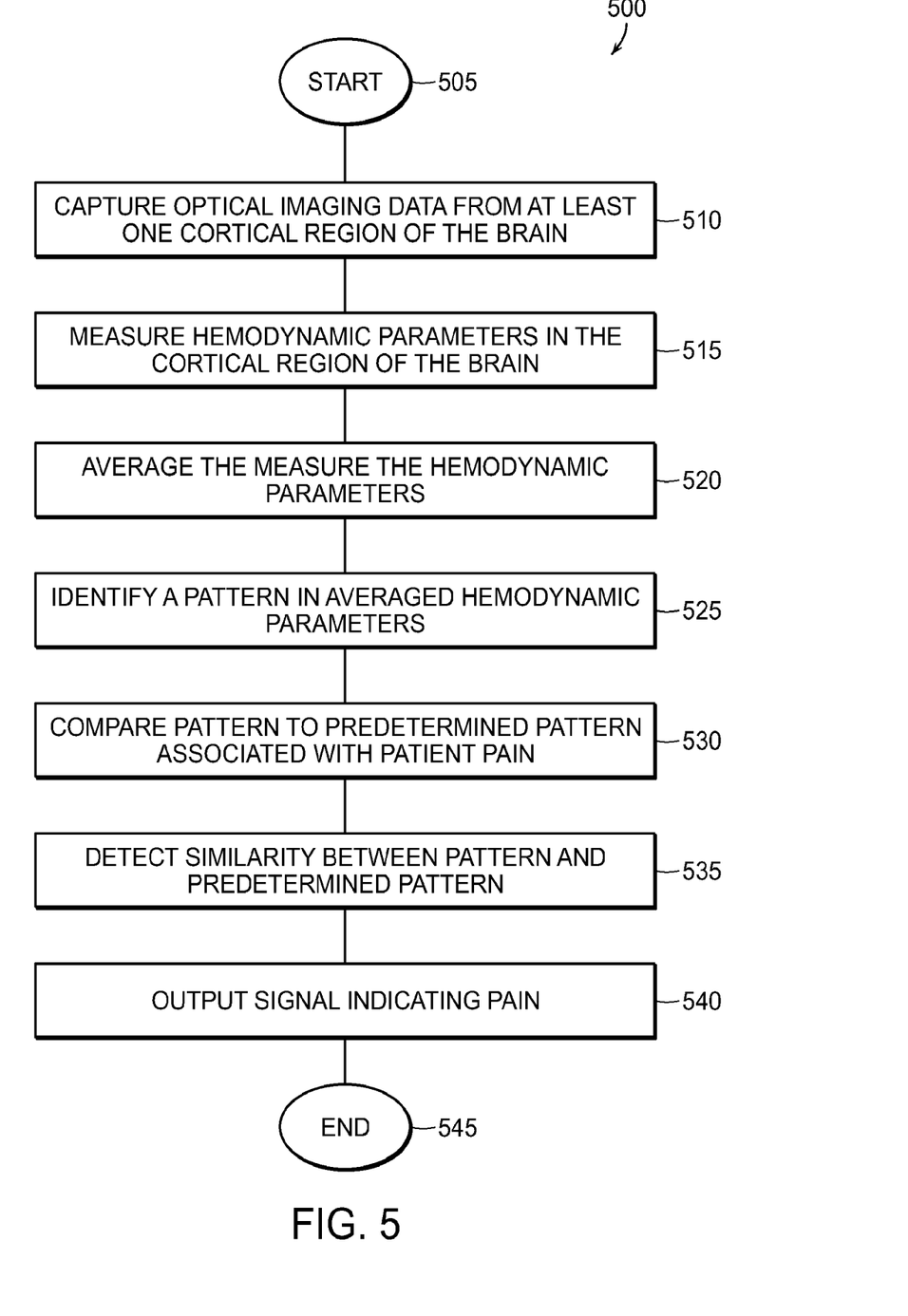
FIG. 5 illustrates an exemplary flowchart of the method that recognizes pain in a patient according to an exemplary embodiment of the present disclosure.

Moreover, FIG. 5 illustrates an exemplary flowchart of process 500 of recognizing pain in a patient during a medical procedure. The process 500 may illustratively start at 505 and continue to 510 wherein optical imaging data may be captured from at least one cortical region of the brain of the non-responsive patient over a period of time, using a functional near-infrared spectroscopy. Furthermore, the process includes in 515 measuring, by a processor, a plurality of hemodynamic parameters in the at least one cortical region of the brain of the non-responsive patient, using the optical imaging data. In 520, the process may include averaging, by the processor, the measured plurality of hemodynamic parameters to reduce background noise and in 525, identifying, by the processor, a pattern in the averaged hemodynamic parameters. In addition, in 530, the process may include comparing, by the processor, the pattern to at least one predetermined pattern associated with patient pain. The process may then include in 535, detecting, by the processor, a similarity between the pattern and the predetermined pattern. Lastly, in 540, outputting, by the processor, a signal indicating patient pain, and then the processor may illustratively end in 545.

Furthermore, the hemodynamic parameters may include oxygenated hemoglobin, deoxygenated hemoglobin, and total hemoglobin. The measuring of the hemodynamic parameter may include measuring, by the processor, oxygenated and deoxygenated hemoglobin to measure blood flow. The at least one cortical region of the brain may be selected from the somatosensory cortex and the prefrontal cortex.

Additionally, the process may further include determining, by the processor, whether a time delay between performing the finger tapping exercise and the variation of electrical stimulus and a point when a peak occurs in blood flow indicates pain in the patient. Furthermore, the at least one predetermined pattern associated with pain may be obtained from control data for the hemodynamic parameter, wherein the control data may be obtained by acquiring the optical imaging data form the at least one cortical region of the brain of a conscious patient. Specifically, the control data may be obtained when a stimulus has not been administered to a patient and includes performing, by the processor, an activity to the patient. The activity performed on the patient may include a finger tapping exercise and a variation of electrical stimulus to inflict pain. In addition, the process may include, administering, by the processor, an anesthetic regimen based on a particular medical procedure toward the patient after obtaining the control data.

In a further embodiment of the present disclosure, a method that evaluates a treatment may include administering, by a processor, the treatment toward a patient and applying a stimulus toward the patient. Furthermore, the process may include acquiring imaging data during the application of the stimulus using a functional near-infrared spectroscopy. In addition, the process may include determining, by the processor, brain activity data representing hemodynamic parameter in a least one cortical region of the brain of the patient, from the imaging data and comparing, by the processor, the brain activity data representing the hemodynamic parameter to control data representing the hemodynamic parameter. The process may further include outputting, by the processor, an indication of patient pain. Additionally, the process may include acquiring, by the processor, control data using the functional near-infrared spectroscopy prior to obtaining the activity imaging data. A determined reduction in the intensity of the hemodynamic parameter from the control data to the imaging data indicates a relative efficiency of the treatment as a pain-relieving treatment.

Methods and systems of the invention may be employed to detect pain and the following non-limiting example is illustrative of the invention.

EXAMPLE

In this study patients were monitored using NIRS during a routine colonoscopy procedure to analyze brain activity during various procedural events. Specifically, pain was induced by stretching the colon during insufflation and characterizing the signal to determine whether the patient experiences pain.

Methods of Example

Subjects

Seventeen healthy adults were recruited from a population of patients undergoing screening colonoscopy. Of the seventeen adults, eleven were male and six were female ranging from ages 36-79. Three data sets were eliminated due to no marked stimulus event and two additional data sets were eliminated due to poor signal quality from patient motion. Thus, twelve data sets were used for analysis wherein the subjects included six males.

Equipment

The subjects were fitted with a TechEn CW6 NIRS imaging system (TechEn, Milford Mass.) and data was recorded using the NIRS imaging system during the duration of the medical procedure. The NIRS imaging system was configured to emit near infrared wavelengths of light to measure changes in cortical deoxyhemoglobin and oxyhemoglobin concentration. Auxiliary channels in the data acquisition system were utilized to mark particular activities such as patient grimacing, patient motion, injection of anesthetic regimens, at the like.

Paradigm

Finger tapping was delivered manually to each patient's hand which was marked for stimulus delivery. The finger tapping was delivered in substantially the same location using substantially the same pressure each time. Intraoperative recordings were collected and markers were placed in the data set, using an auxiliary data acquisition channel, for the duration of each cardiac ablation event. In particular, three variations of electrical stimulus were applied to the patient.

The patients were all provided with similar anesthetic regimen including midazolam and Demerol. However, the recall of the colonoscopy by some patients is an indication of variation in response to the anesthetic regimen based on difference in the interactions of clinical evaluation, pharmacogemonic, or gender differences.

In addition, nociceptive signals may not be effectively blocked by the anesthetic regiment. Effective blockade of nociceptive signaling is dependent on the intensity, duration, and repetition of afferent signals. Although a patient may not express pain during a medical procedure, nociceptive pathways may still be activated as a result of repeated stimuli which may cause local or central sensitization to occur, thus resulting in pain after the medical procedure.

Data Analysis

Analysis was performed using Homer2 software and the analysis has been previously published Gagnon L, Perdue K, Greve D N, et al Improved recovery of the hemodynamic response in diffuse optical imaging using short optode separations and state-space modeling. Neuroimage 2011; 56:1362-71.

Results

Figure 1:
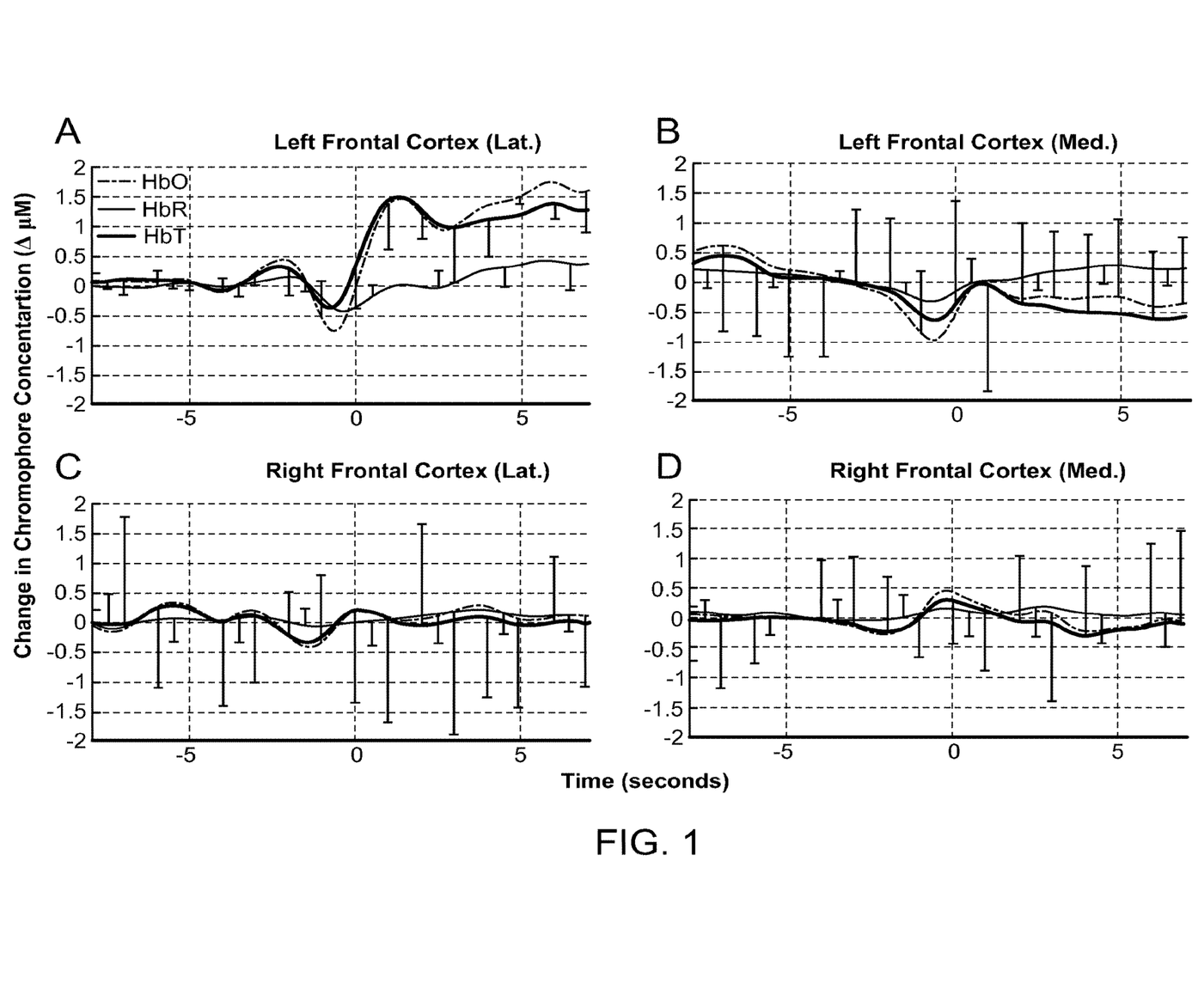
FIG. 1 illustrates an exemplary graph showing hemodynamic response functions observed at various cortices according to an exemplary embodiment of the present disclosure.
Figure 2:
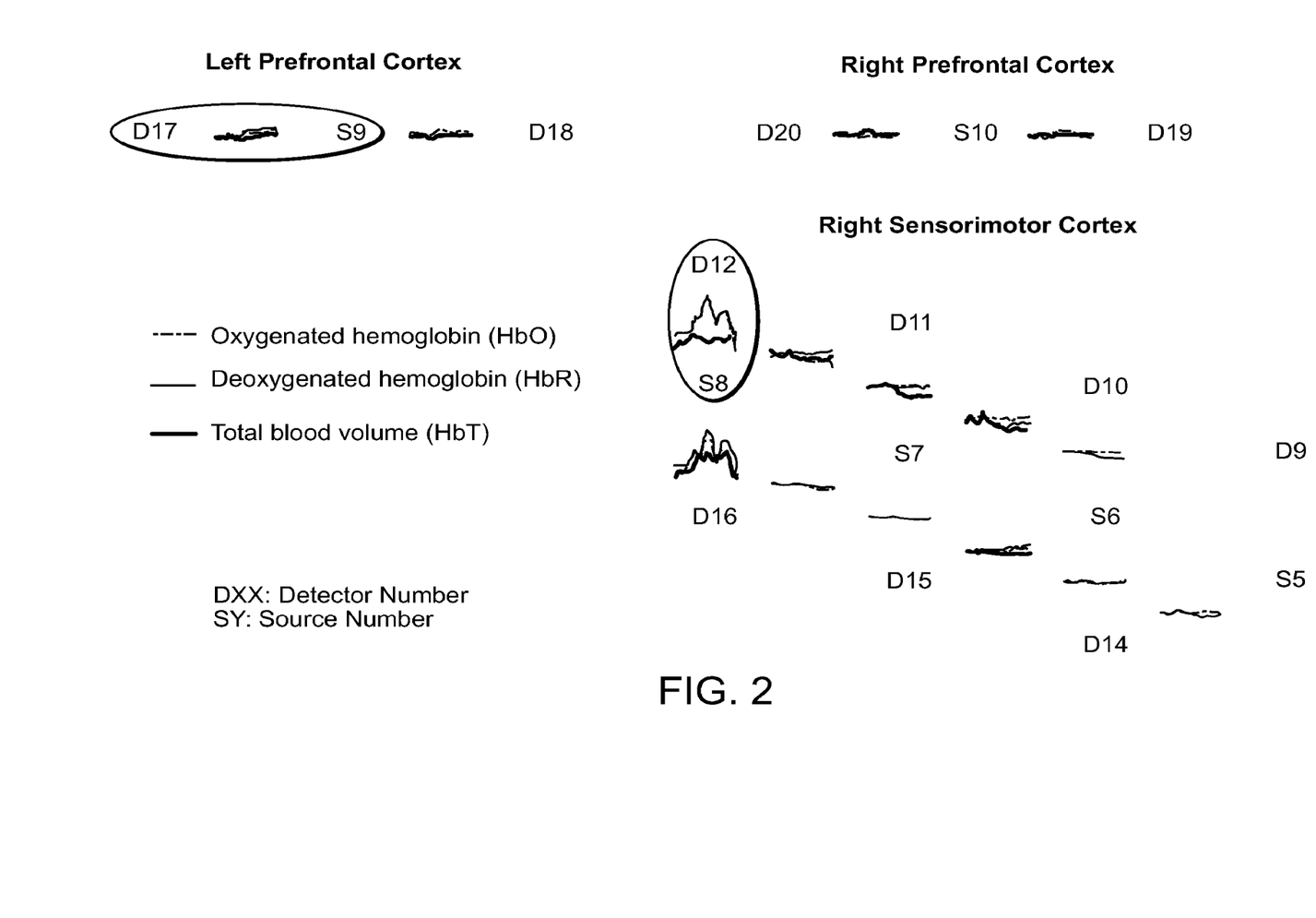
FIG. 2 illustrates an exemplary graph of hemodynamic response functions according to an exemplary embodiment of the present disclosure.

Relative brain activity was measured across the prefrontal and somatosensory cortices as shown in FIG. 2. Specifically, FIG. 2 illustrates that the medial somatosensory cortex experienced the greatest change in oxygenation and hemoglobin. The bi-phasic response, as shown in FIG. 1, shows HbO and HbT peaks occurring about every 4 seconds, observed in two somatosensory channels, thereby indicating patient pain.

Figure 3:
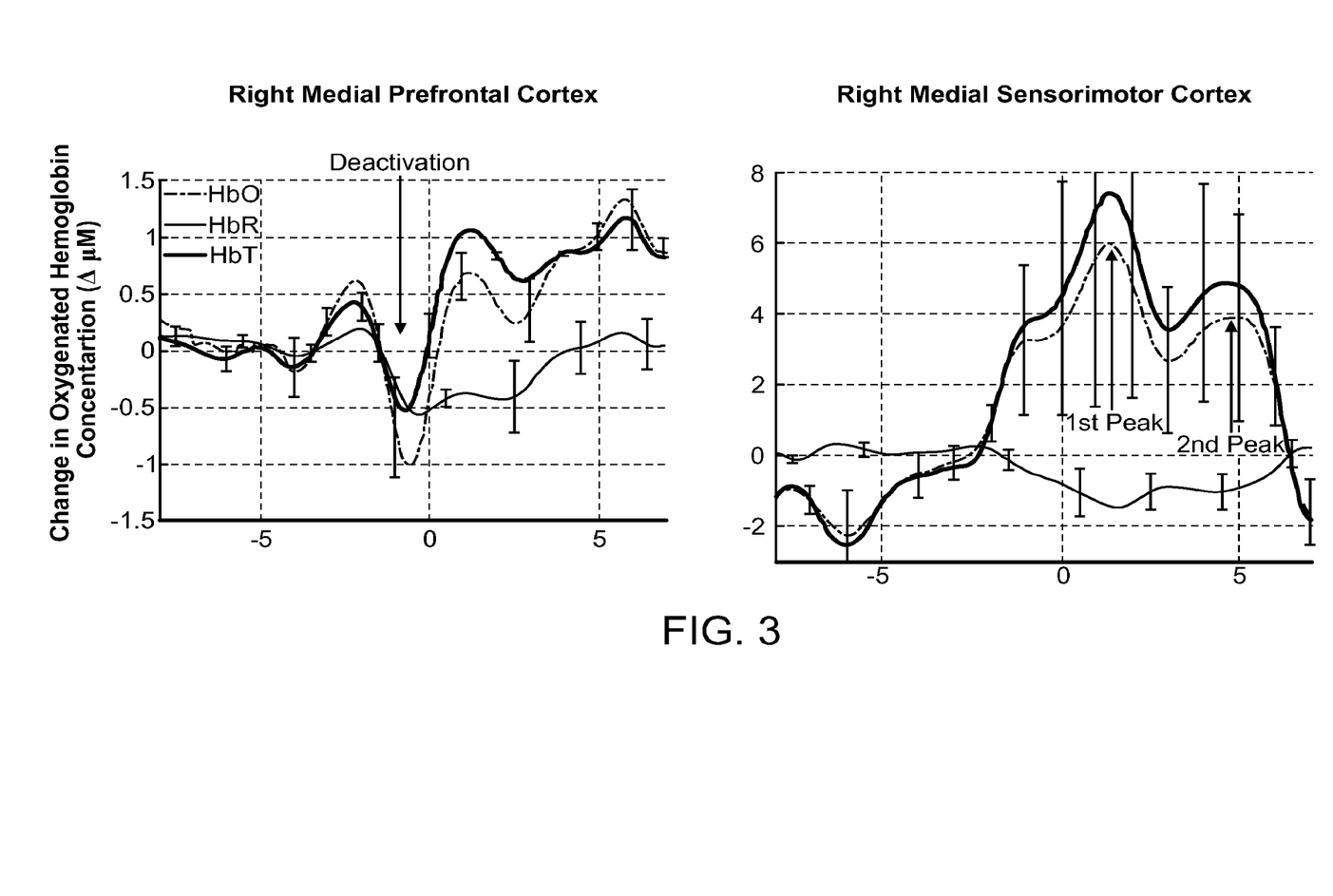
FIG. 3 illustrates exemplary graphs of hemodynamic response functions observed at right medial prefrontal cortices and somatosensory cortices according to an exemplary embodiment of the present disclosure.

In the prefrontal cortex, the bilateral decrease in HbO and HbT prior to time zero, and corresponding rise to a peak value about 3 seconds later indicates patient pain, as shown in FIGS. 1 and 3. In particular, FIG. 3 shows the decrease in oxygenated hemoglobin, at approximately 2 seconds prior to the grimace response, indicating deactivation of medical prefrontal cortex neurons following the initiation of the pain stimulus, based on the approximately 6 second time-to-negative peak observed in studies where pain was applied with known timing.

Discussion

The group average hemodynamic response function observed in the prefrontal and somatosensory cortices is similar to the results obtained in previous near-infrared studies that monitor the brain during controlled pain stimulation. The time offset may be the result of the different methods of marking the stimulus onset. Furthermore, significant delay may be caused by the reaction time of a sedated patient corresponding to a negative-time shift in the hemodynamic response. The increase in signal intensity may indicate increased pain intensity.

The results in the above example show a signal of alterations in brain neuronal activity that corresponds with the timing of insufflation of the colon and facial grimacing thus indicating that the medial procedure produces alterations in brain processing during the elicitation of pain. Furthermore, the NIRS signal observed was similar to the signal produced by a pain stimuli in the same region on a patient not subjected to anesthetics.

Furthermore a reproducible signal over the frontal cortex was observed and although sensory representation of the colon is present in the primary somatosensory cortex, and a potential area to focus on recording a nociceptive signal, the area is substantially small and as a result was only observable in a subset of the patient population. Furthermore, the observed signal was obtained from observation of grimace in the patients, thus indicating that a movement may be observed in conjunction with pain.

The observed signal in frontal cortex is similar to the phasic thermal and electrical stimulation further suggesting that the signal indicates patient pain. Based on to the results obtained in this study, afferent pain signals are shown to be processed in the brain of patients undergoing colonoscopy with moderate sedation.

The present pain detector apparatus and methods can provide continuous monitoring of neural activity related to pain experienced during medical procedures. That apparatus may provide control of analgesic load to improve patient intraoperative comfort and decrease postoperative pain. In addition, the measure or detection of pain may be used to evaluate the effectiveness of pharmaceuticals for a variety of conditions.

What is claimed is:

1. A method for identifying an indicator of pain in a non-responsive patient, comprising:
    performing, by a processor, functional near-infrared spectroscopy imaging upon a responsive patient, thereby obtaining control near-infrared spectroscopy imaging data for the patient;
    administering, by the processor, a stimulus to the responsive patient;
    performing, by the processor, functional near-infrared spectroscopy imaging upon the responsive patient, thereby obtaining pain indicia near-infrared spectroscopy imaging data for the patient experiencing a stimulus;
    administering, by the processor, a sedative to the responsive patient, thereby rendering the patient non-responsive;
    administering, by the processor, an invasive procedure to the non-responsive patient;
    obtaining, by the processor, functional near-infrared spectroscopy imaging data from the nonresponsive patient during performance of the invasive procedure;
    measuring one or more hemodynamic parameters in a medial prefrontal cortex region of the brain of the non-responsive patient using the imaging data;
    averaging the measured one or more hemodynamic parameters to reduce background noise and identifying a pattern in the averaged hemodynamic parameters;
    comparing, by the processor, the averaged hemodynamic parameters in the near-infrared spectroscopy imaging data obtained from the nonresponsive patient during performance of the invasive procedure to the control or pain indicia near-infrared spectroscopy imaging data obtained from the patient;
    identifying, by the processor, a pattern match between the identified pattern in the averaged hemodynamic parameters of the near-infrared spectroscopy imaging data obtained from the nonresponsive patient during performance of the invasive procedure and the pain indicia near-infrared spectroscopy imaging data obtained from the patient, thereby identifying an indicator of pain in the non-responsive subject; and
    altering, by the processor, the invasive procedure or administering a pain-reducing agent to the non-responsive patient for whom an indicator of pain is identified,
    wherein using the imaging data one or more hemodynamic parameters are measured in the medial prefrontal cortex region of the brain of the non-responsive patient and the measured plurality of hemodynamic parameters are averaged to identify a pattern of decreased functional near-infrared spectroscopy signals in the medial prefrontal cortex of the patient which is compared with a predetermined pattern associated with evoked pain, and
    wherein the predetermined pattern indicating pain comprises a plurality of sequential peaks in blood flow over time.

2. The method of claim 1, wherein functional near-infrared spectroscopy imaging data is obtained from at the least one cortical region of the brain of the non-responsive patient.

3. The method of claim 1 wherein the hemodynamic parameters include one or more of oxygenated hemoglobin, deoxygenated hemoglobin, and total hemoglobin.

4. The method of claim 1 wherein measuring at least one hemodynamic parameter includes measuring oxygenated and deoxygenated hemoglobin to measure blood flow.

5. The method of claim 1 wherein the invasive procedure is a colonoscopy.

6. The method of claim 1 wherein the control near-infrared spectroscopy imaging data are obtained by acquiring optical imaging data from the medial prefrontal cortex of the brain of the responsive patient.

7. The method of claim 6 wherein acquiring the optical imaging data includes performing an activity to the patient.

8. The method of claim 7 wherein the activity is a finger tapping exercise and a variation of electrical stimulus.

9. A system that identifies an indicator of pain in a non-responsive patient, comprising:
    a functional near-infrared spectroscope configured to capture (a) control and pain indicia optical imaging data from at least one cortical region of the brain of a patient while responsive and (b) optical imaging data from a medial prefrontal cortex region of the brain of the patient when the patient is rendered non-responsive; and a processor programmed to:

perform functional near-infrared spectroscopy imaging upon a responsive patient, thereby obtaining control near-infrared spectroscopy imaging data for the patient;

administer a stimulus to the responsive patient;

perform functional near-infrared spectroscopy imaging upon the responsive patient, thereby obtaining pain indicia near-infrared spectroscopy imaging data for the patient experiencing a stimulus;

administer a sedative to the responsive patient, thereby rendering the patient non-responsive;

administer an invasive procedure to the non-responsive patient;

obtain functional near-infrared spectroscopy imaging data from the nonresponsive patient during performance of the invasive procedure;

measure one or more hemodynamic parameters in a medial prefrontal cortex region of the brain of the non-responsive patient using the imaging data;

average the measured one or more hemodynamic parameters to reduce background noise and identify a pattern in the averaged hemodynamic parameters;

compare the averaged hemodynamic parameters in the near-infrared spectroscopy imaging data obtained from the nonresponsive patient during performance of the invasive procedure to the control or pain indicia near-infrared spectroscopy imaging data obtained from the patient;

identify a pattern match between the identified pattern in the averaged hemodynamic parameters of the near-infrared spectroscopy imaging data obtained from the nonresponsive patient during performance of the invasive procedure and the pain indicia near-infrared spectroscopy imaging data obtained from the patient, thereby identifying an indicator of pain in the non-responsive subject; and alter the invasive procedure or administering a pain-reducing agent to the non-responsive patient for whom an indicator of pain is identified, wherein using the imaging data one or more hemodynamic parameters are measured in the medial prefrontal cortex region of the brain of the non-responsive patient and the measured plurality of hemodynamic parameters are averaged to identify a pattern of decreased functional near-infrared spectroscopy signals in the medial prefrontal cortex of the patient which is compared with a predetermined pattern associated with evoked pain, and wherein the predetermined pattern indicating pain comprises a plurality of sequential peaks in blood flow over time.

10. The system of claim 9 wherein the hemodynamic parameters include one or more of oxygenated hemoglobin, deoxygenated hemoglobin, and total hemoglobin.

11. The system of claim 9 wherein the processor is further configured to control an analysis exercise and a variation of electrical stimulus on the nonresponsive patient to inflict a level of pain.

12. The system of claim 9 wherein the processor is further configured to determine whether a time delay between performing an analysis exercise and the variations of electrical stimulus and a point when a peak occurs in blood flow indicates pain in the patient.

13. The method of claim 1 wherein the patient is non-communicative.

* * * * *

UNITED STATES PATENT AND TRADEMARK OFFICE
CERTIFICATE OF CORRECTION

| | |
|---|---|
| PATENT NO. | : 10,806,395 B2 |
| APPLICATION NO. | : 14/777323 |
| DATED | : October 20, 2020 |
| INVENTOR(S) | : David Borsook et al. |

It is certified that error appears in the above-identified patent and that said Letters Patent is hereby corrected as shown below:

On the Title Page

Item (72) Inventors reads:
David Borsook
Lino Becerra

Should read:
David Borsook
Lino Becerra, Cambridge, MA
Barry Kussman, Waban, MA

Signed and Sealed this
Tenth Day of September, 2024

Katherine Kelly Vidal
*Director of the United States Patent and Trademark Office*